United States Patent [19]

Sumita et al.

[11] Patent Number: 5,404,227
[45] Date of Patent: Apr. 4, 1995

[54] CONTAINER INSPECTING APPARATUS HAVING ROTARY INDEXING APPARATUS

[75] Inventors: Masahiko Sumita; Takahiro Mukai, both of Yokohama, Japan

[73] Assignee: Kirin Techno-System Corporation, Yokohama, Japan

[21] Appl. No.: 111,893

[22] Filed: Aug. 26, 1993

[30] Foreign Application Priority Data

Aug. 29, 1992 [JP] Japan .................................. 4-254137

[51] Int. Cl.⁶ ............................................ G01N 21/90
[52] U.S. Cl. .................................. 356/428; 198/343.1; 198/476.1; 198/480.1
[58] Field of Search ............... 198/343.1, 343.2, 474.1, 198/476.1, 377, 378; 356/240, 428; 250/223 B; 209/526, 527, 701

[56] References Cited

U.S. PATENT DOCUMENTS

| | | |
|---|---|---|
| 2,317,559 | 4/1943 | Stout . |
| 3,479,514 | 11/1969 | Kidwell .............................. 209/526 |
| 3,528,544 | 9/1970 | Noguchi et al. . |
| 4,511,025 | 4/1985 | Nakayama .......................... 198/377 |
| 5,074,397 | 12/1991 | Mukai et al. . |
| 5,121,827 | 6/1992 | Ribordy ............................. 198/377 |

FOREIGN PATENT DOCUMENTS 0303175  2/1989  European Pat. Off. .

OTHER PUBLICATIONS

Patent Abstracts of Japan, vol. 9, No. 44 (P-337) [1767], Feb. 23, 1985, JP-A-59 183 351, Oct. 18, 1984.

*Primary Examiner*—Richard A. Rosenberger
*Assistant Examiner*—Robert Kim
*Attorney, Agent, or Firm*—Oblon, Spivak, McClelland, Maier, & Neustadt

[57] ABSTRACT

A container inspecting apparatus for inspecting containers such as vials, ampuls, or the like has an inlet star wheel rotatable for admitting containers successively, and an outlet star wheel rotatable for discharging the containers successively. A plurality of feed units are movable along a circular path for successively receiving containers from the inlet star wheel, stopping the containers in respective inspecting positions, and successively transferring the containers to the outlet star wheel. A plurality of inspecting devices, each comprising an illuminating unit and an imaging unit, are disposed respectively in the inspecting positions for inspecting the containers in the respective inspecting positions. The feed units are intermittently moved along the circular path by a feeding and indexing device. A support mechanism is vertically mounted on each of the feed units for supporting bottoms of the containers on the feed units. The support mechanism is rotated to rotate the containers about their own axes while the containers are being inspected by the inspecting devices.

12 Claims, 7 Drawing Sheets

CONTAINER INSPECTING APPARATUS HAVING ROTARY INDEXING APPARATUS

BACKGROUND OF THE INVENTION

1. Field of the Invention

The present invention relates to a container inspecting apparatus for inspecting small cylindrical containers, which may be empty or filled, for defects on their entire external surface, and more particularly to a container inspecting apparatus for inspecting frozen dry vials.

2. Description of the Prior Art

There have been proposed various container inspecting apparatus for inspecting transparent small cylindrical containers such as vials, ampules, or the like. For example, Japanese laid-open patent publications Nos. 1-291110 and 64-38640, respectively disclose a container inspecting apparatus, in which a vial is intermittently fed from a conveyor to a vial gripper, then intermittently fed to an inspecting position by the vial gripper, and intermittently discharged to the conveyor after being inspected in the inspecting position.

The vial gripper comprises a rotary disk for contacting a side of the vial near its bottom, a pair of rollers opposing the rotary disk for contacting the side of the vial near its bottom, and a support plate for supporting the bottom of the vial. The rollers are interconnected by a spring for holding the vial. The support plate has an elongated hole for viewing the bottom of the vial therethrough with a camera. In the inspecting position, the vial is held at rest against the feeding movement, rotated about its own axis by the rotary disk, and viewed at its top, side, and bottom during rotation.

However, since the vial is intermittently supplied to and discharged from the vial gripper, the vial movement is relatively unstable. The container inspecting apparatus has a plurality of vial grippers which start and stop moving at the same time. Therefore, the container inspecting apparatus vibrates during operation, and its operating speed cannot be increased.

Another problem of the vial grippers is that inasmuch as the rotary disk and the rollers contact the sides of the vial, an imaging system for imaging the vial with transmitted light is comparatively complex in structure.

Japanese laid-open utility model publications Nos. 3-36948, 3-36949, 3-36950 and Japanese laid-open patent publication No. 1-152347 also disclose a container inspecting apparatus, respectively. In the disclosed container inspecting apparatus, vials are successively supplied from a conveyor to a vial gripper, then successively supplied to inspecting positions by the vial gripper, and successively discharged to the conveyor after being inspected in the inspecting position. Each vial is not stopped in the inspecting position, and for inspecting the entire circumferential wall of the vial, it is rotated about its own axis successively through certain angles while it is being transported.

The vial is gripped by a vacuum pad having a semicircular horizontal cross section which is held against a side surface of the vial. The vial is rotated about its own axis by a rotating roller or belt that is placed in abutment against the side of the vial.

The vial is viewed by successively rotating it through the angles until the full circumferential wall of the vial is imaged. Therefore, the conventional container inspecting apparatus requires a plurality of cameras for imaging a certain region of the vial, and hence are relatively large in size. Light that would be transmitted through the vial cannot be used to inspect the vial because about half of the entire circumferential wall of the vial is concealed by the pad held against the vial in the vial gripper.

SUMMARY OF THE INVENTION

It is therefore an object of the present invention to provide a container inspecting apparatus which is capable of successively feeding containers to inspecting positions, stopping the containers against feeding movement in the inspecting positions, rotating the containers about their own axis for inspecting the full circumferential walls of the containers, and successively discharging the containers after they have been inspected.

Another object of the present invention is to provide a container inspecting apparatus which has a plurality of feed units, for feeding respective containers, which are prevented from starting and stopping moving in a plurality of inspecting positions at the same time, and which has no members that would otherwise contact and conceal outer side surfaces of containers.

According to the present invention, there is provided a container inspecting apparatus comprising an inlet star wheel rotatable for introducing containers successively; an outlet star wheel rotatable for discharging containers successively; a plurality of feed units movable along a circular path for successively receiving containers from the inlet star wheel, stopping the containers in respective inspecting positions, and successively transferring the containers to the outlet star wheel; a plurality of inspecting devices disposed respectively in the inspecting positions for inspecting the containers in the respective inspecting positions; a feeding and indexing device for intermittently feeding the feed units along the circular path; a support mechanism vertically mounted on each of the feed units for supporting bottoms of the containers on the feed units; and rotating means for rotating the support mechanism to rotate the containers about their own axes.

With the above structure, containers that have successively been introduced by the inlet star wheel are transferred to the feed units, and the bottoms of the containers are supported by the support mechanism. The containers on the respective feed units are fed along the circular path by the feeding and indexing device, and stopped in the inspecting positions. While in the inspecting positions, the containers are rotated about their own axes by the rotating means, and the full circumferential walls of the containers are inspected by the inspecting devices which are composed of an illuminating unit and an imaging unit, respectively. After being inspected, the containers are successively discharged by the outlet star wheel.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Figure 1:
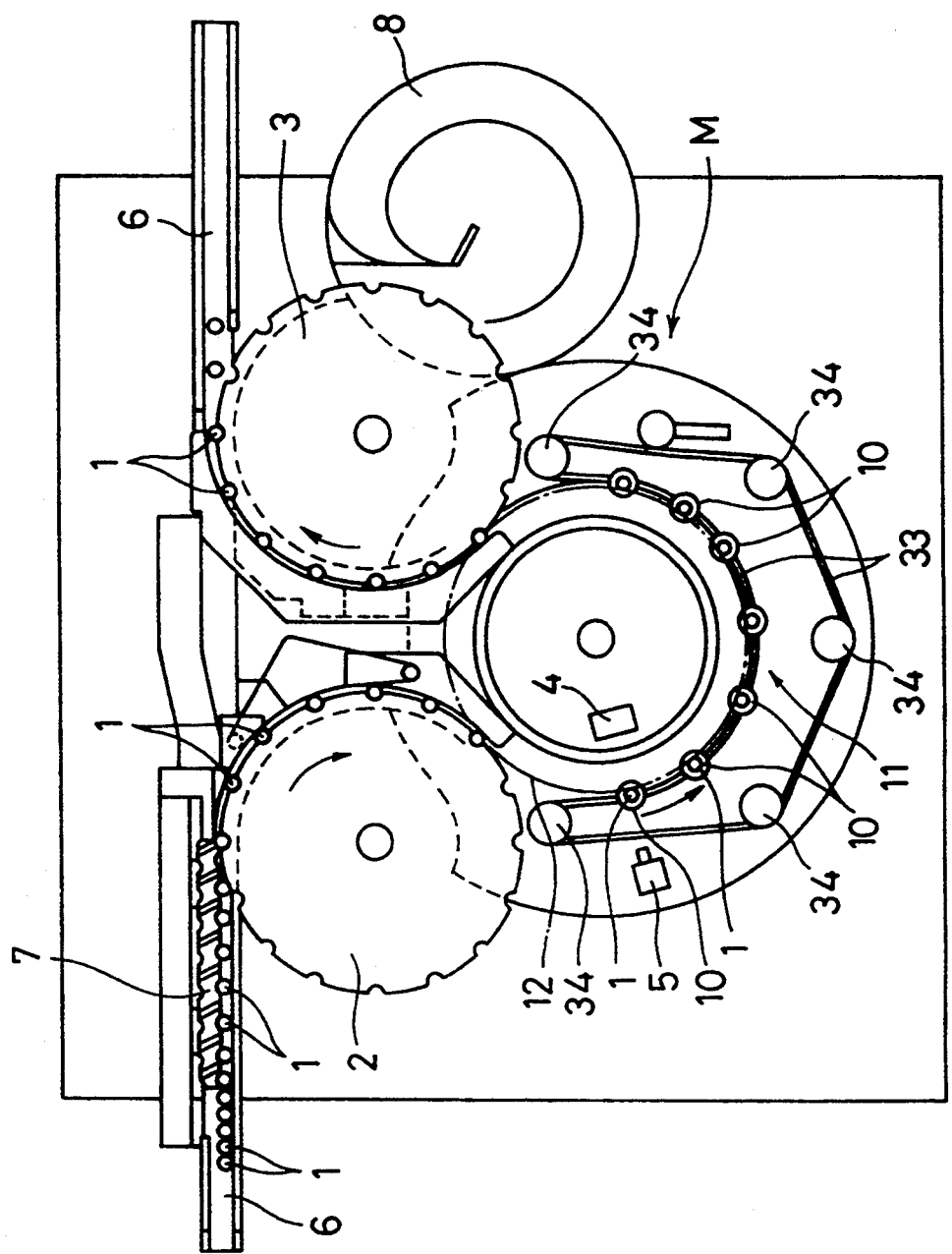
FIG. 1 is a plan view of a container inspecting apparatus according to an embodiment of the present invention.

As shown in FIG. 1, a container inspecting apparatus M comprises: an inlet star wheel 2 for successively introducing vials 1; an outlet star wheel 3 for successively discharging the vials 1; a plurality of feed units 10 movable along a circular path 12 for receiving the vials 1 from the inlet star wheel 2, stopping them in respective inspecting positions, and discharging the vials 1 to the outlet star wheel 3; a plurality of sets of an illuminating unit 4 and an imaging unit 5 (only one set is shown in FIG. 1) disposed in the respective inspecting positions; and a feeding and indexing device 11 for intermittently moving the feed units 10 along the circular path 12.

A conveyor 6 is positioned adjacent to the inlet star wheel 2 and the outlet star wheel 3, and an infeed screw 7 is disposed adjacent to the inlet star wheel 2. Vials 1 are successively supplied from the conveyor 6 to the infeed screw 7, which cause the vials 1 to be spaced at constant intervals. Thereafter, the vials 1 are transferred from the infeed screw 7 to the inlet star wheel 2, from which the vials 1 are transferred to the respective feed units 10.

A turntable 8 is located adjacent to the outlet star wheel 3. After the vials 1 have been inspected, those vials 1 which do not have defects are fed from the outlet star wheel 3 to the conveyor 6 for transfer to a next process, and those vials 1 which have defects are transferred from the outlet star wheel 3 to the turntable 8 where they are stocked.

The feed units 10 and the feeding and indexing device 11 will be described below with reference to FIGS. 2 through 5.

Figure 2:
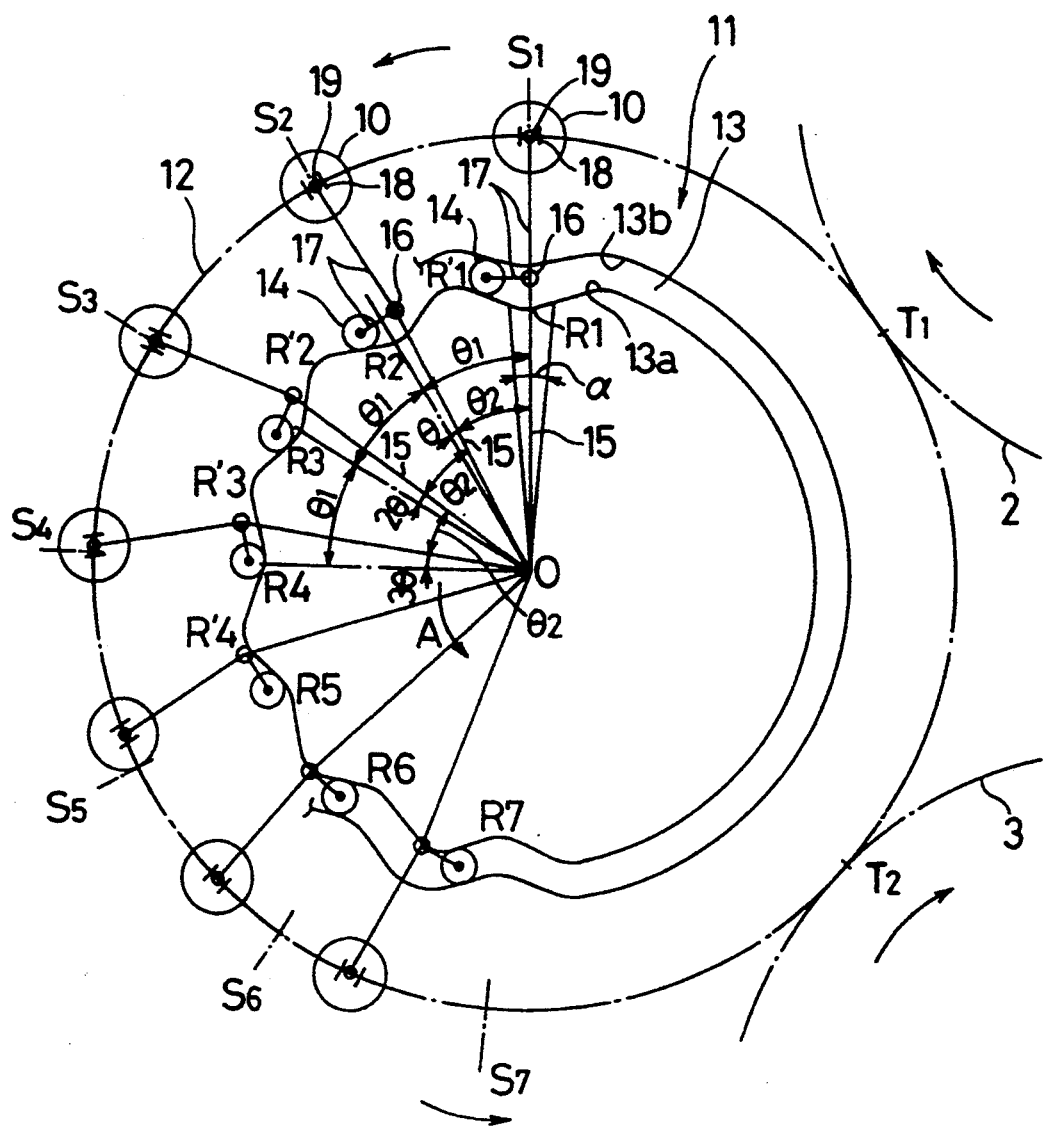
FIG. 2 is a schematic plan view of a feeding and indexing device in the container inspecting apparatus.

In FIG. 2 the feed units 10 are movable along the circular path 12 by the feeding and indexing device 11. The feeding and indexing device 11 comprises: a substantially circular cam groove 13; a plurality of cam followers 14 movable along the cam groove 13; a plurality of radial drive arms 15 rotatable about the center 0 of the cam groove 13; and a plurality of driven arms 17 rotatably connected to the respective drive arms 15 and coupled to the respective cam followers 14.

The cam groove 13 is fixedly positioned radially inwardly of and concentrically with the circular path 12. The cam groove 13 includes an arcuate portion on half of its full extent and also has an inner cam profile 13a and an outer cam profile 13b which are radially spaced from each other and have a wavy configuration. The inner and outer cam profiles 13a, 13b jointly have a plurality of valleys R1-R7 and a plurality of mountains R'1-R'6 alternating with the valleys R1-R7. The cam followers 14 are in the form of rollers provided in unison with the respective feed units 10. The cam followers 14 are movable in contact with the inner and outer cam profiles 13a, 13b.

The drive arms 15 which are rotatable about the center O of the cam groove 13 are associated respectively with the feed units 10. More specifically, the drive arms 15 have respective radially outer ends to which respective inverted L-shaped driven arms 17 are angularly movably connected at their axes by respective rotary bearings 16. The driven arms 17 have respective hands connected to the respective cam followers 14. The driven arms 17 also have respective radial hands that are operatively connected to the respective feed units 10 by respective linear sliding bearings 18 such that the distance between the axes of the driven arms 17, i.e., the position of the rotary bearings 16 and the respective feed units 10, is variable. Rotary bearings 19 are interposed between the linear sliding bearings 18 and the feed units 10 for making the feed units 10 rotatable with respect to the linear sliding bearings 18.

The feeding and indexing device 11 receives, at a contact point $T_1$, a vial 1 on one of the feed units 10 from the inlet star wheel 2 that is rotating continuously. The drive arms 15 are rotating at a constant speed in the direction indicated by the arrow A. While a cam follower 14 is moving in the arcuate portion of the cam groove 13, the feed unit 10 associated with the cam follower 14 moves along the circular path 12 at a constant speed. As the cam follower 14 approaches the valley R1 in the wavy configuration of the cam groove 13, the driven arm 17 is angularly moved counterclockwise about the rotary bearing 16 with respect to the drive arm 15. Therefore, the driven arm 17 is tilted further forwardly along the circular path 12 from an outward radial extension of the drive arm 15. The feed unit 10 approaches an inspecting position $S_1$ and hence is decelerated. The feed unit 10 is stopped when it reaches the inspecting position $S_1$. Each of the inspecting positions $S_1$ through $S_7$ is associated with an illuminating unit and an imaging unit (not shown in FIG. 2).

When the drive arm 15 and the radial hand of the driven arm 17 are radially aligned with each other, they are in a central position during an interval in which the feed unit 10 is in the inspecting position $S_1$. The feed unit 10 remains stopped in the inspecting position $S_1$ insofar as the drive arm 15 is positioned within an angular range $\alpha$ across the central position.

While the driven arm 17 is angularly moving about the inspecting position $S_1$, the feed unit 10 continuously remains at rest in the inspecting position $S_1$. During angular movement of the driven arm 17 about the inspecting position $S_1$, the distance between the feed unit 10 and the rotating axis of the driven arm 7 (the position of the rotary bearing 16) varies, and the variation in the distance is absorbed by the linear sliding bearing 18 that connects the feed unit 10 to the driven arm 17. As the cam follower 14 approaches the peak of the mountain R'1 upon further rotation of the drive arm 15, the feed unit 10 starts leaving the inspecting position $S_1$. Continued movement of the cam follower 14 past the mountain R'1 toward the valley R2 causes the feed unit 10 to approach the outward radial extension of the drive arm 15, i.e., to be accelerated. When the drive arm 15 is superposed on the mountain R'1, the speed of the feed unit 10 is maximum.

Thereafter, the feed unit 10 moves toward a next inspecting position $S_2$, and repeats the above operation. After the feed unit 10 moves past a last inspecting position $S_7$, the feed unit 10 is accelerated. Then, the feed unit 10 moves at a constant speed, and discharges the vial 1 onto the outlet star wheel 3 at a contact point $T_2$.

In the feeding and indexing device shown in FIG. 2, a pitch angle $\theta_1$ is formed at the center O between the center of the valley R1 corresponding to the inspecting position $S_1$ and the center of the valley R2 corresponding to the inspecting position $S_2$, and a pitch angle $\theta_2$ is formed at the center O between the rotary bearing 16 corresponding to the inspecting position $S_1$ and the center of the rotary bearing 16 corresponding to the inspecting position $S_2$. These pitch angles $\theta_1$, $\theta_2$ differ from each other by an angle $\theta$, and are not equal to each other ($\theta_1 \neq \theta_2$). Put another way, the feeding and indexing device includes a cam having a periodic configuration substantially centered at a center of rotation of the circular path of the feed units and cooperating with a cam follower for guiding intermittent movement of the feed units, wherein the period of the configuration of the cam in the circumferential direction of the circular path differs by an angle $\theta$ from a spacing of the feed units along the circular path. The pitch angle $\theta_1$ may be made greater or smaller than the pitch angle $\theta_2$.

The instant a drive arm 15 is aligned with the center of the valley R1 at the inspecting position $S_1$, another drive arm 15 is angularly spaced from the center of the valley R2 by an angle $\theta$ at the inspecting position $S_2$, and still another drive arm 15 is angularly spaced from the center of the valley R3 by an angle $2\theta$ at the inspecting position $S_3$. Generally, a drive arm 15 is angularly spaced from the center of a valley Rn by an angle $(n-1)\theta$ at an inspecting position $S_n$ (n is an integer of 1 or greater). Therefore, the feed units 10 operate at slightly different times.

If the angle $\theta$ corresponds to a rotating angle per unit time, then a drive arm 15 is aligned with the center of the valley R2 at the inspecting position $S_2$ upon elapse of the unit time from the instant the parts are positioned as shown in FIG. 2. Upon elapse of another unit time, a drive arm 15 is aligned with the center of the valley R3 at the inspecting position $S_3$. Consequently, the starting and stopping times of the respective feed units 10 differ by the unit time.

Figure 3:
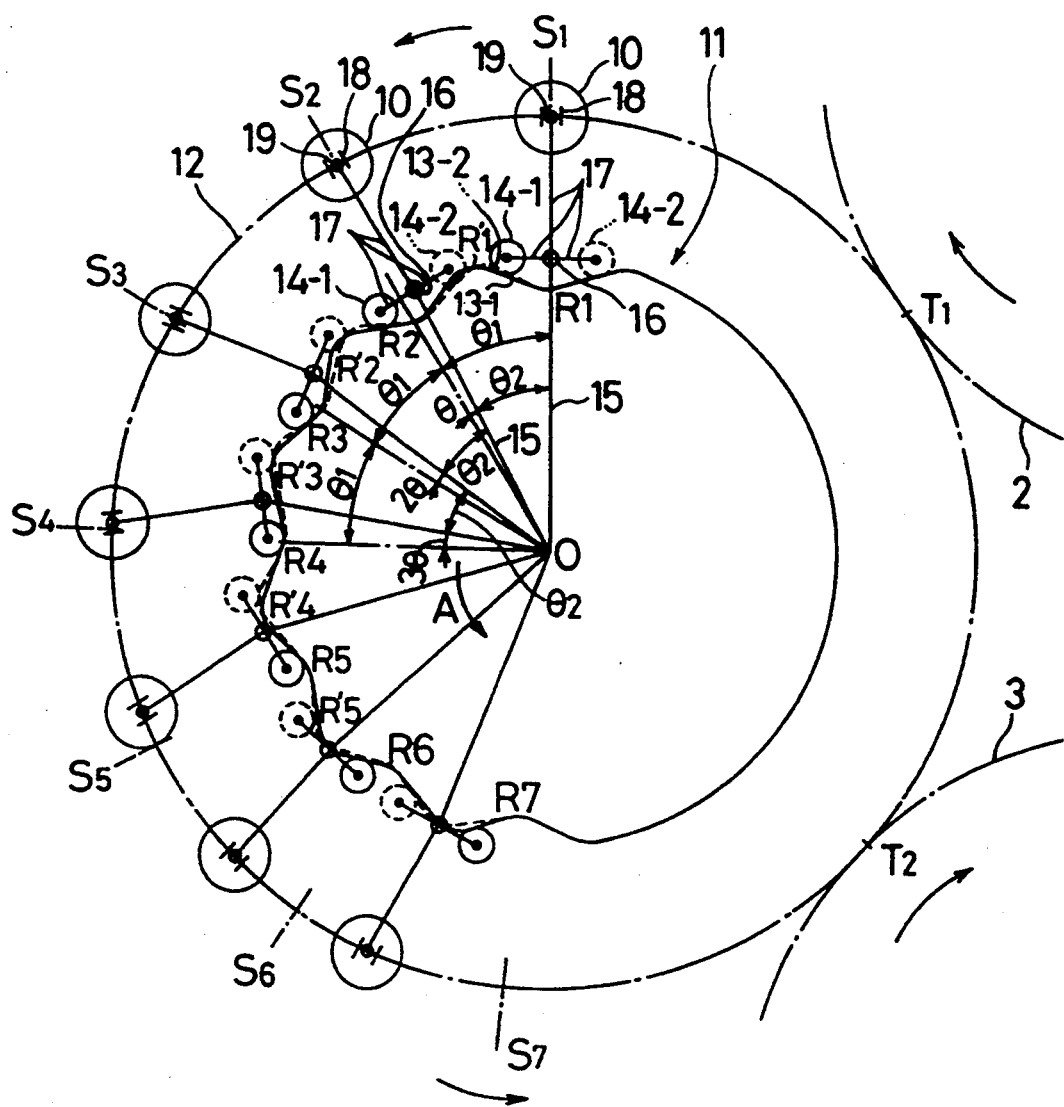
FIG. 3 is a schematic plan view of a modified feeding and indexing device.

FIG. 3 shows a modification of the feeding and indexing device shown in FIG. 2. The modification is with respect to the cam, the cam follower, and the driven arms. The other details of the modified feeding and indexing device shown in FIG. 3 are the same as those of the feeding and indexing device shown in FIG. 2. As shown in FIG. 3, the modified feeding and indexing device has two cams 13-1, 13-2 positioned one on the other, with the cam 13-2 being indicated by broken lines. The cams 13-1, 13-2 are conjugate cams with respect to each other.

The modified feeding and indexing device also has a plurality of pairs of cam followers 14-1, 14-2 held in contact with the respective cams 13-1, 13-2, with the cam followers 14-2 being indicated by broken lines. The drive arms 15, the feed units 10, and the cam followers 14-1, 14-2 are operatively coupled to each other by T-shaped driven arms 17. The driven arms 17 are operatively connected to the respective feed units 10 by respective linear sliding bearings 18 serving as connecting members. The modified feeding and indexing device shown in FIG. 3 operates in the same manner as the feeding and indexing device shown in FIG. 2.

Each of the feeding and indexing devices shown in FIGS. 2 and 3 has a plurality of drive arms 15. These drive arms 15 may be replaced with a unitary drive plate, which may support rotary bearings 16 which in turn support driven arms 17 rotatably.

Figure 4:
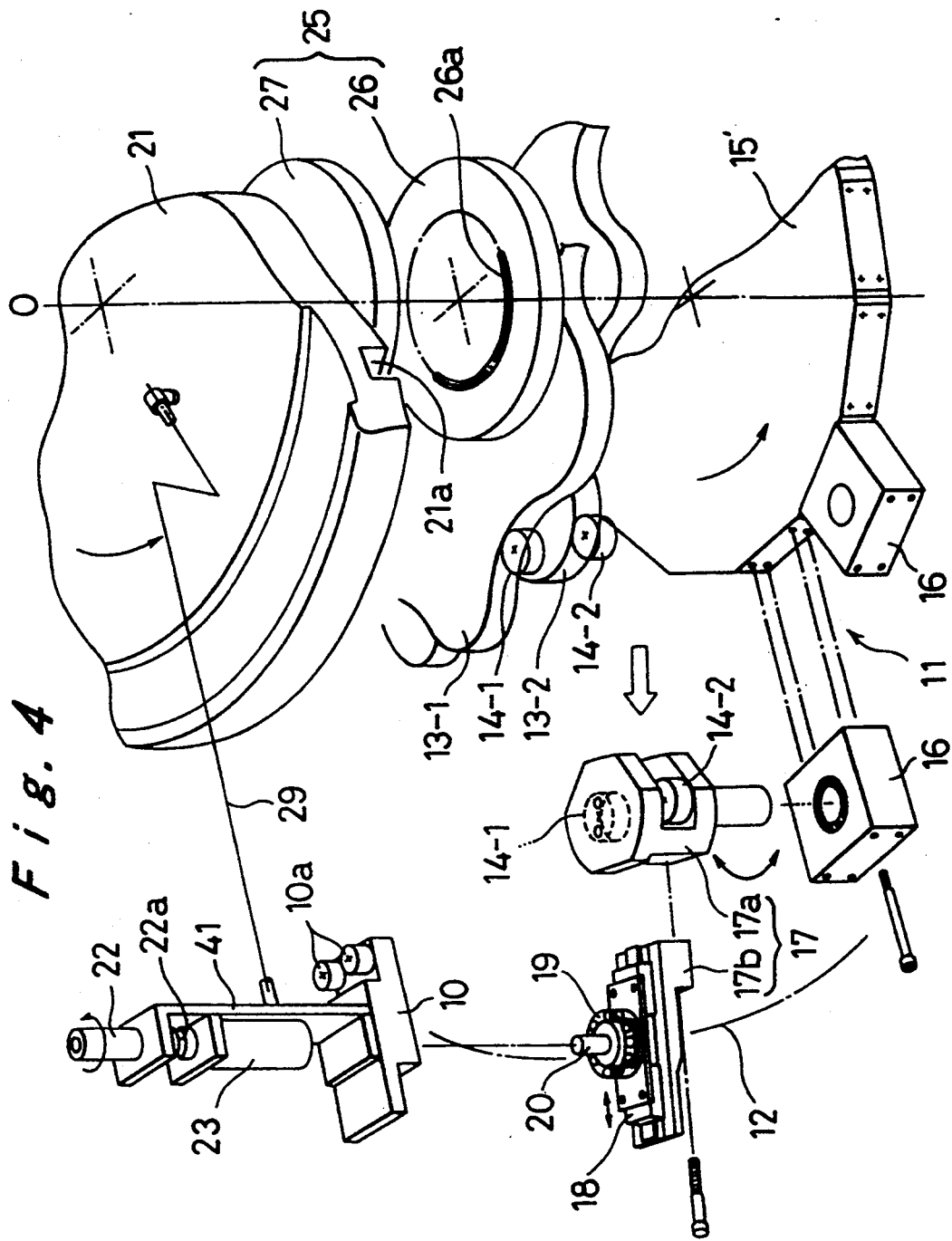
FIG. 4 is an exploded perspective view of an example in which the feeding and indexing device shown in FIG. 3 is employed.
Figure 5:
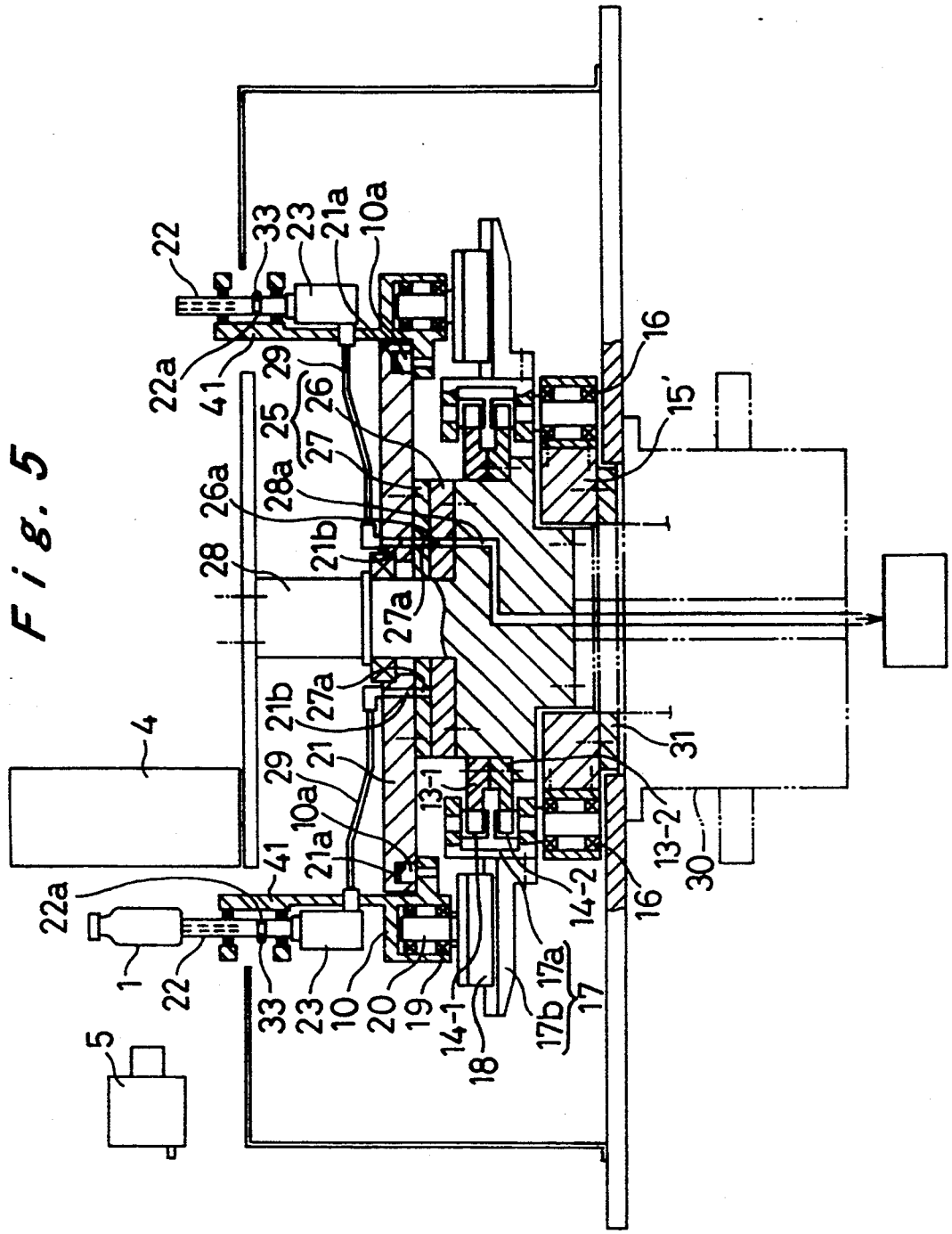
FIG. 5 is a vertical cross-sectional view of the container inspecting apparatus according to an embodiment of the present invention.

FIGS. 4 and 5 show an example in which the feeding and indexing device shown in FIG. 3 is incorporated.

In FIG. 4, each of the feed units 10 has a pair of guide rollers 10a rollingly engaging in a circular groove 21a formed in one surface of a turret disk 21 having the center O. Therefore, the feed units 10 are movable along the circular path 12, which is defined by the circular groove 21a. The two conjugate cams 13-1, 13-2 are fixed radially inwardly of the circular path 12, i.e., the circular groove 21a, in concentric relationship thereto. Each pair of cam followers 14-1, 14-2, which are movable in contact with the respective conjugate cams 13-1, 13-2, is associated with one of the feed units 10.

The feeding and indexing device also has a unitary drive plate 15' with the rotary bearings 16 mounted on its outer circumferential edge. The driven arms 17 are rotatably supported by the respective rotary bearings 16. Each of the driven arms 17 has a base 17a rotatably fitted in one of the rotary bearings 16 and a radial extension 17b fastened to the base 17a by bolts. The base 17a and the radial extension 17b make up a T-shaped driven arm 17. As shown in FIG. 5, the drive plate 15' is coupled to an annular output shaft 31 of a speed reducer 30, so that the drive plate 15' can be rotated at a constant speed by the speed reducer 30. The cam followers 14-1, 14-2 are fixed to the base 17a of the driven arm 17, which is angularly movable with respect to the rotary bearing 16 as it follows the cam profiles of the cams 13-1, 13-2. The driven arm 17 and the corresponding feed unit 10 are operatively coupled to each other by the linear sliding bearing 18. The rotary bearing 19 is interposed between the linear sliding bearing 18 and the feed unit 10, so that the feed unit 10 is rotatable about a shaft 20 supported by the rotary bearing 19 with respect to the linear sliding bearing 18.

The feeding and indexing device shown in FIGS. 4 and 5 operates in the same manner as the feeding and indexing devices shown in FIGS. 2 and 3.

A support mechanism coupled to the feed units 10 and a vacuum system of the support mechanism will be described below with reference to FIGS. 4 and 5.

The support mechanism includes a plurality of vertical suction pipes 22 rotatably supported on the respective feed units 10 by respective bracket 41 mounted on the feed units 10. The suction pipes 22 have respective upwardly open upper ends for supporting vials 1 thereon, and respective lower ends coupled to respective rotary joints 23. A slide valve 25, which comprises a fixed plate 26 and a rotating plate 27 that is rotatably disposed on the fixed plate 26, is disposed between the drive plate 15' and the turret disk 21 concentrically with the feeding and indexing device 11. The fixed plate 26 is securely supported on a fixed support 28 disposed upwardly of the drive plate 15'. The fixed plate 26 has a port 26a in the form of an arcuate slot defined therein about its center. The port 26a communicates with a vacuum source through a communication hole 28a defined in the support 28.

The rotating plate 27 has a plurality of circular ports 27a defined therein at spaced intervals for communication with the port 26a. The ports 27a are held in communication with corresponding communication holes 21b defined in the turret disk 21 that rotates in unison with the rotating plate 27. The communication holes 21b communicate with the respective rotary joints 23 through respective tubes 29, so that a vacuum can be developed in the suction pipes 22 by the vacuum source.

The port 26a in the fixed plate 26 arcuately extends over an angular interval between the contact point $T_1$ (see FIGS. 2 and 3) where the feed units 10 contact the inlet star wheel 2 and the contact point $T_2$ (see FIGS. 2 and 3) where the feed units 10 contact the outlet star wheel 3. The suction pipes 22 coupled to the respective feed units 10 attract vials 1 placed on their upper ends under a vacuum developed in the suction pipes 22, and keep attracting the respective vials 1 so long as the feed units 10 are positioned in the angular interval of the port 26a.

The suction pipes 22 have respective grooves 22a formed in the outer circumferential surfaces of lower portions thereof. The grooves 22a receive a rotatable belt 33 which, as shown in FIG. 1, is held against the suction pipes 22 and trained around a plurality of pulleys 34 that are rotatable about their own axes by a drive source such as a motor. When the pulleys 34 are rotated, the belt 33 travels to rotate the suction pipes 22 about their own axes, for thereby rotating the vials 1 supported respectively on the suction pipes 22 about their own axes through an angle of 360° or greater in the inspecting positions $S_1$-$S_7$.

As shown in FIG. 5, one illuminating unit 4 and one imaging unit 5 are positioned on each side of the vial 1 supported on one of the suction pipes 22. Although not shown, other illuminating and imaging units are also positioned on each side of the other vials 1 supported on the other suction pipes 22. Since the vial 1 is supported at its bottom on the suction tube 22 and nothing is held against the outer side surface of the vial 1, the entire circumferential wall of the vial 1 can easily be inspected with light horizontally transmitted through the vial 1 by the illuminating unit 4 and the imaging unit 5. Each of the suction tubes 22 has an outside diameter substantially smaller than the outside diameter of the vial 1. Therefore, the round edge of the bottom of the vial 1 is exposed to view for easy inspection.

A modified support mechanism will be described below with reference to FIGS. 6 and 7.

Figure 6:
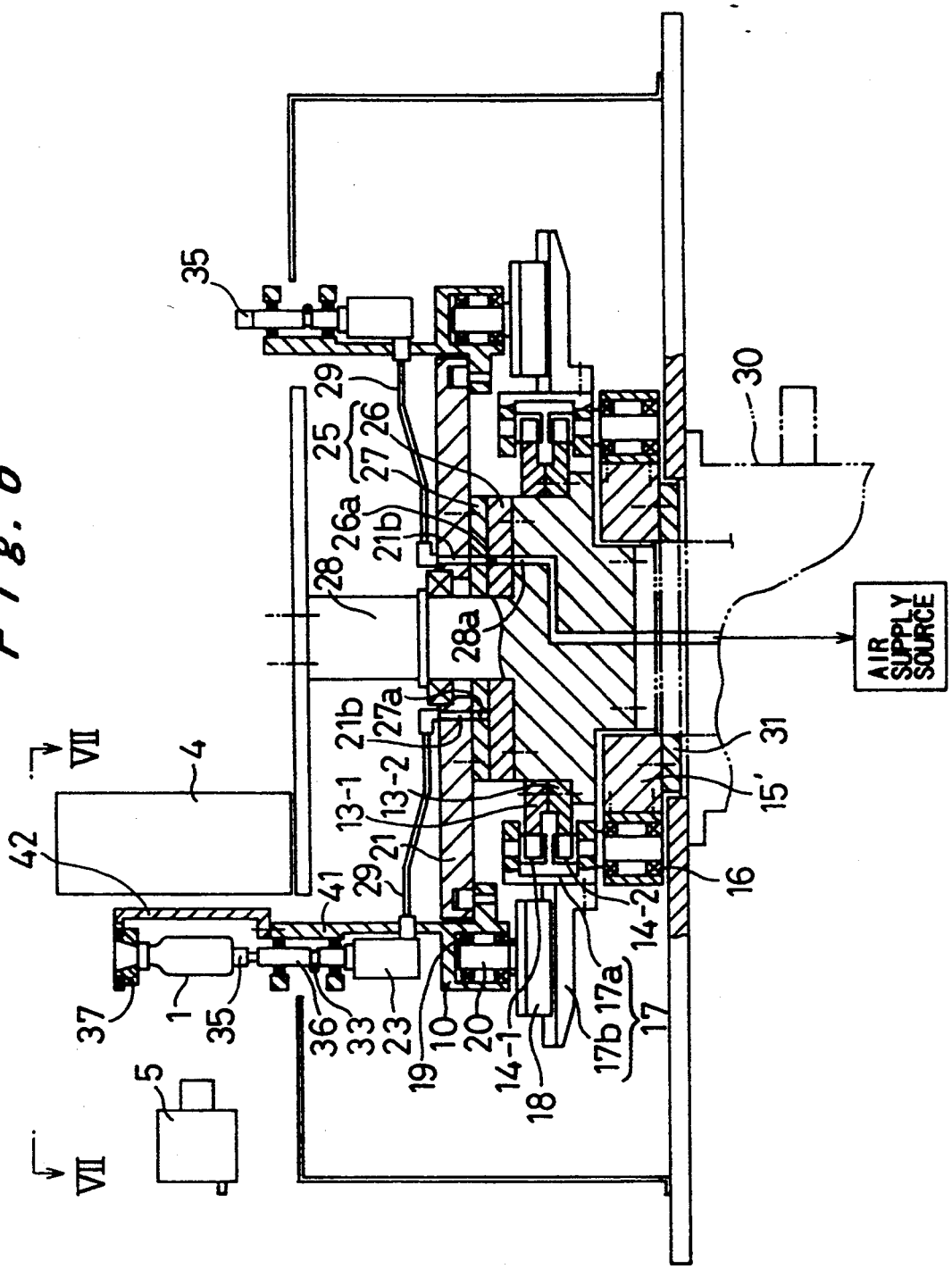
FIG. 6 is a vertical cross-sectional view of a modified support mechanism in the container inspecting apparatus.

As shown in FIG. 6, the modified support mechanism has a vertical support rod 35 and a presser plate 37, associated with each of the feed units 10, for supporting a vial 1 vertically therebetween. The support rod 35 for supporting the bottom of the vial 1 is rotatably mounted on each feed unit 10 by the bracket 41 coupled to the feed unit 10. The support rod 35 is connected to a single-acting air cylinder 36 that communicates with one of the communication holes 21b of the turret disk 21 through the rotary Joint 23 and the tube 29. The presser plate 37 is rotatably supported by a support column 42 that is vertically fixed to the bracket 41. As shown in FIG. 7, the support column 42 is positioned so as not to interfere with the illuminating unit 4 and the imaging unit 5.

The port 26a formed in the fixed plate 26 and the ports 27a formed in the rotating plate 27 are held in communication with an air supply source through the communication hole 28a formed in the support 28. When air under pressure is supplied from the air supply source, the air cylinder 36 is actuated to push the support rod 35 upwardly to grip the vial 1 vertically between the support rod 35 and the presser plate 37.

Figure 7:
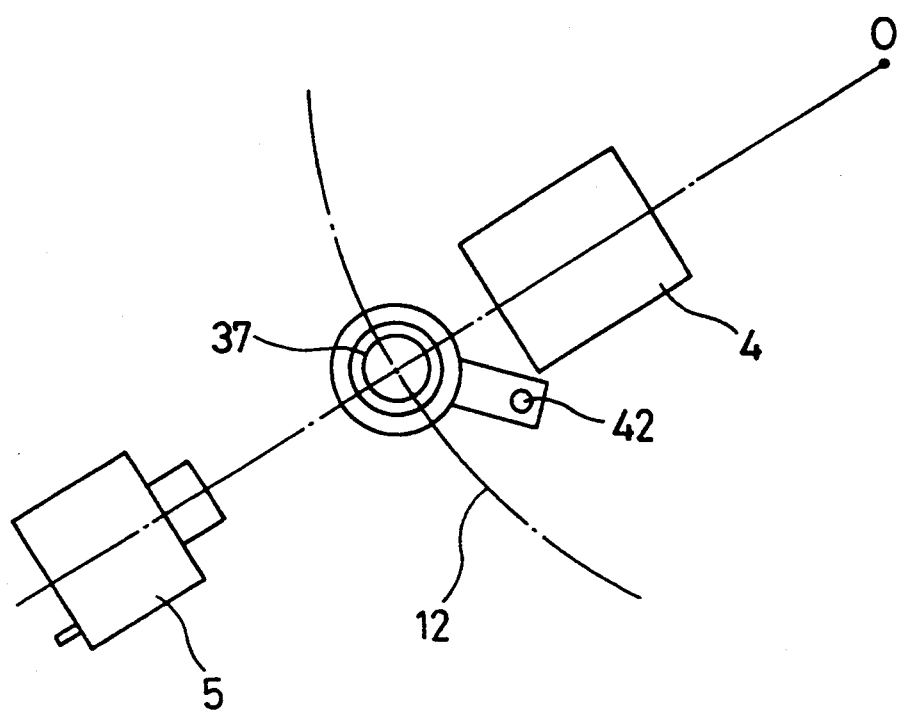
FIG. 7 is a plan view taken along line VII—VII of FIG. 6.

The other details of the modified support mechanism shown in FIGS. 6 and 7 are identical to those of the support mechanism shown in FIGS. 4 and 5, and will not be described in detail below.

Operation of the container inspecting apparatus M with the support mechanism shown in FIGS. 4 and 5 will briefly be described below.

Vials 1 introduced by the inlet star wheel 2 are successively transferred to the respective feed units 10, and the bottoms of the vials 1 are supported on the respective suction pipes 22 of the feed units 10. Then, the vials 1 on the feed units 10 are successively fed along the circular path 12 and successively stopped in the inspecting positions $S_1$-$S_7$. While the vial 1 is at rest in each of the inspecting positions $S_1$-$S_7$, it is rotated about its own axis by the belt 33. During rotation of the vial 1, the outer surface of the vial 1 and the content, if any, of the vial 1 are inspected by the illuminating unit 4 and the imaging unit 5. Specifically, the illuminating unit 4 shines light on the vial 1, and the imaging unit 5 images the vial 1 with light transmitted through the vial 1 to check the vial 1 for any defect on its full circumferential wall and in its content, if any. Thereafter, the vial 1 is discharged from the container inspecting apparatus M by the outlet star wheel 3. Any vials 1 including the content that are found acceptable are fed from the outlet star wheel 3 onto the conveyor 6 for transfer to a next process. Any vials 1 including the content that are found defective are rejected by the outlet star wheel 3 and discharged onto the turntable 8.

With the arrangement of the present invention, as described above, vials or containers 1 to be inspected are successively introduced and stopped in the respective inspecting positions $S_1$-$S_7$, in which the vials 1 are rotated about their own axes for inspection of their entire outer circumferential walls. After being inspected, the vials 1 are successively discharged from the container inspecting apparatus M. The vials 1 can successively be introduced smoothly into the container inspecting apparatus M and discharged smoothly from the container inspecting apparatus M. Only one pair of illuminating and imaging units is required to inspect the full circumferential wall of a vial in at least one of the inspecting positions $S_1$-$S_7$.

Since nothing conceals the outer side surface of each vial 1 as it is supported in each of the inspecting positions $S_1$-$S_7$, the full circumferential wall of the vial 1 can be inspected with light transmitted through the vial 1 by the illuminating and imaging units 4, 5. Thus, the illuminating and imaging units 4, 5 may be relatively simple in structure.

The feed units 10 for successively feeding the respective vials 1 do not start and stop moving simultaneously in the inspecting positions $S_1$-$S_7$. Consequently, the container inspecting apparatus M is prevented from vibrating during its operation, allows the vials 1 to be inspected or otherwise processed smoothly, and can operate at high speed.

Although certain preferred embodiments of the present invention have been shown and described in detail, it should be understood that various changes and modifications may be made therein without departing from the scope of the appended claims.

What is claimed is:

1. A container inspecting apparatus comprising:
   a rotatable inlet star wheel for introducing containers successively;
   a rotatable outlet star wheel for discharging the containers successively;

a plurality of feed units movable along a circular path for successively receiving the containers from said inlet star wheel, stopping the containers in respective inspecting positions, and successively transferring the containers to said outlet star wheel;

an inspecting device disposed in each of said respective inspecting positions for inspecting a container placed in said each inspecting position;

a feeding and indexing device for intermittently moving said feed units along said circular path such that said feed units are stopped in said respective inspecting positions at mutually different times;

a support mechanism vertically mounted on each of said feed units for supporting the bottom of said container placed on said feed units; and rotating means for rotating said support mechanism to rotate the container about its own axes.

2. A container inspecting apparatus according to claim 1, wherein said feeding and indexing device comprises:

cam means having a wavy cam profile on a partly circumferential surface;

a plurality of cam followers movable along said wavy cam profile;

drive arm means rotatable about a center of said cam means;

a plurality of driven arms operatively coupled to said drive arm means and to said cam followers at respective junction points; and a plurality of connecting members operatively coupled to said driven arms and to corresponding feed units, each of said connecting members being provided for allowing the respective distance between a rotating axis of said driven arm and a corresponding feed unit to vary;

wherein when said drive arm means rotates about the center of said cam means, said driven arms are angularly rotated respectively about said junction points by said cam followers moving along said wavy cam profile so as to stop said feed units in said inspecting positions and to move said feed units between said inspecting positions.

3. A container inspecting apparatus according to claim 2, wherein said wavy cam profile includes a plurality of mountains and a plurality of valleys alternating with said mountains, and a pitch angle defined between adjacent ones of said mountains or valleys is different from a pitch angle defined between adjacent ones of said junction points of said drive arm means and said driven arms.

4. A container inspecting apparatus according to claim 1, wherein said support mechanism comprises a plurality of suction pipes, each suction pipe being rotatably mounted on said feed unit for supporting a bottom of a container thereon, a rotary joint connected to said suction pipe, a slide valve disposed concentrically with said feeding and indexing device, and a common vacuum source connected to said suction pipe through said rotary joint and said slide valve, for developing a vacuum in said suction pipe to attract the bottom of the container on the suction pipe.

5. A container inspecting apparatus according to claim 4, wherein said slide valve comprises a fixed plate and a rotating plate rotatably mounted on said fixed plate, said rotating plate has a plurality of ports defined therein which are communicated with said suction pipes, respectively, and said fixed plate has an arcuate port defined therein connected to said vacuum source and extending in an angular interval between a contact point between each of said feed units and said inlet star wheel, and a contact point between each of said feed units and said outlet star wheel.

6. A container inspecting apparatus according to claim 1, wherein said support mechanism comprises a plurality of vertically movable support rods rotatably mounted on said feed units, respectively, a plurality of presser plates rotatably supported on said feed units, respectively, a plurality of air cylinders connected to said support rods, respectively, a plurality of rotary joints connected to said air cylinders, respectively, a slide valve disposed concentrically with said feeding and indexing device, and an air supply source connected to said air cylinders through said rotary joints and said slide valve, for supplying air under pressure to said air cylinders to push said support rods toward said presser plates, respectively, to grip the containers between said support rods and said presser plates, respectively.

7. A container inspecting apparatus according to claim 6, wherein said slide valve comprises a fixed plate and a rotating plate rotatably mounted on said fixed plate, said rotating plate has a plurality of ports defined therein which are communicated with said air cylinders, and said fixed plate has an arcuate port defined therein connected to said air supply source and extending in an angular interval between a contact point between each of said feed units and said inlet star wheel, and a contact point between each of said feed units and said outlet star wheel.

8. A container inspecting apparatus according to claim 1, wherein said rotating means comprises a belt engaging said support mechanism.

9. A container inspecting apparatus according to claim 1, wherein at least one of said inspecting devices comprises an illuminating unit for illuminating the container supported on one of said feed units and an imaging unit for recording an image of the container with light transmitted through the container.

10. The container inspecting apparatus according to claim 1 wherein said feeding and indexing device comprises a cam having a periodic configuration substantially centered at a center of rotation of said circular path and cooperating with a cam follower for guiding said intermittent movement of said feed units, wherein the period of the configuration of said cam in the circumferential direction of said circular path differs by an angle $\Theta$ from a spacing of said feed units along said circular path.

11. The container inspecting apparatus according to claim 10 wherein said periodic configuration includes a series of mountains and valleys, wherein said valleys are circumferentially spaced by an angular spacing which differs by an angle $\Theta$ from a spacing of said feed units along said circular path.

12. A container inspecting apparatus comprising:

a rotatable inlet star wheel for introducing containers successively;

a rotatable outlet star wheel for discharging the containers successively;

a plurality of feed units movable along a circular path for successively receiving the containers from said inlet star wheel, stopping the containers in respective inspecting positions, and successively transferring the containers to said outlet star wheel;

an inspecting device disposed in each of said respective inspecting positions for inspecting a container placed in said each inspecting position;

a feeding and indexing device for intermittently moving said feed units along said circular path such that said feed units are stopped in said respective inspecting positions at mutually different times;

a support mechanism vertically mounted on each of said feed units for supporting the bottom of said container placed on said feed units, said support mechanism including suction tubes positioned to engage bottoms of said containers and having outside diameters substantially smaller than outside diameters of said containers such that edges of said bottoms of said containers are visible for inspection; and rotating means for rotating said support mechanism to rotate the container about its own axes.

* * * * *